US011707250B2

(12) United States Patent
Campagna et al.

(10) Patent No.: US 11,707,250 B2
(45) Date of Patent: Jul. 25, 2023

(54) FAULT MONITORING APPARATUS AND METHOD FOR OPERATING A MEDICAL DEVICE

(71) Applicant: Siemens Healthcare GmbH, Erlangen (DE)

(72) Inventors: Swen Campagna, Engelthal (DE); Thorsten Speckner, Erlangen (DE); Wolfgang Gösswein, Effeltrich (DE); Carsten Prinz, Baiersdorf (DE); Stephan Churt, Hersbruck (DE); Bernd Erbe, Lauf a.d. Pegnitz (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/512,079

(22) Filed: Oct. 27, 2021

(65) Prior Publication Data

US 2022/0160324 A1    May 26, 2022

(30) Foreign Application Priority Data

Nov. 24, 2020   (DE) ..................... 10 2020 214 736.1

(51) Int. Cl.
*A61B 6/00* (2006.01)
*A61B 5/055* (2006.01)

(52) U.S. Cl.
CPC .............. *A61B 6/586* (2013.01); *A61B 5/055* (2013.01)

(58) Field of Classification Search
CPC ................................ A61B 6/586; A61B 5/055
See application file for complete search history.

(56) References Cited

U.S. PATENT DOCUMENTS

| 7,127,371 B2 * | 10/2006 | Duckert ................. | G16H 40/40 702/179 |
| 2004/0181368 A1 * | 9/2004 | Breunissen .............. | A61B 6/56 702/184 |
| 2005/0080596 A1 * | 4/2005 | Duckert ................. | G16H 40/40 702/184 |

(Continued)

FOREIGN PATENT DOCUMENTS

| DE | 102005008502 A1 | 8/2006 |
| DE | 102016206398 A1 | 10/2017 |

OTHER PUBLICATIONS

German Office Action for German Application No. 10 2020 214 736.1 dated Jun. 1, 2021.

*Primary Examiner* — Dixomara Vargas
(74) *Attorney, Agent, or Firm* — Lempia Summerfield Katz LLC

(57) ABSTRACT

The disclosure relates to a method for operating a medical device, (e.g., an imaging apparatus such as an X-ray device or magnetic resonance tomography unit), and a fault monitoring apparatus for carrying out the method. The fault monitoring apparatus is connected to the medical device via a signal connection. In the method, the fault monitoring apparatus receives an item of status information from the medical device and stores the item of status information in a system state. Further, the fault monitoring apparatus compares the stored system state with a predetermined target state, and, depending on the comparison, releases a function of the medical device, wherein the predetermined target state has a successfully executed function test.

17 Claims, 2 Drawing Sheets

1 Magnetic resonance tomography unit
10 Magnetic unit
11 Field magnet
12 Gradient coils
14 Body coil
16 Patient tunnel
20 Control unit
21 Gradient controller
22 Radio frequency unit
23 Controller
25 Signal bus
30 Patient couch
33 Connecting lead
36 Positioning unit
50 Local coil
60 Fault monitoring apparatus
100 Patient

(56) References Cited

U.S. PATENT DOCUMENTS

| | | | | |
|---|---|---|---|---|
| 2008/0082661 A1* | 4/2008 | Huber | ............... | H04L 41/0681 |
| | | | | 709/224 |
| 2010/0011251 A1* | 1/2010 | Mannar | ............... | G16H 40/40 |
| | | | | 714/E11.178 |
| 2011/0160786 A1* | 6/2011 | Stubbs | ............... | A61N 1/37 |
| | | | | 607/7 |
| 2013/0086573 A1* | 4/2013 | Moritzen | ............... | G06F 8/65 |
| | | | | 717/171 |
| 2016/0188828 A1* | 6/2016 | Klingenberg | ......... | G16H 40/40 |
| | | | | 348/175 |
| 2017/0299667 A1* | 10/2017 | Bielmeier | ............ | G01R 33/288 |
| 2019/0307335 A1* | 10/2019 | Bruce | ............... | A61B 5/7405 |

\* cited by examiner

1 Magnetic resonance tomography unit
10 Magnetic unit
11 Field magnet
12 Gradient coils
14 Body coil
16 Patient tunnel
20 Control unit
21 Gradient controller
22 Radio frequency unit
23 Controller
25 Signal bus
30 Patient couch
33 Connecting lead
36 Positioning unit
50 Local coil
60 Fault monitoring apparatus
100 Patient

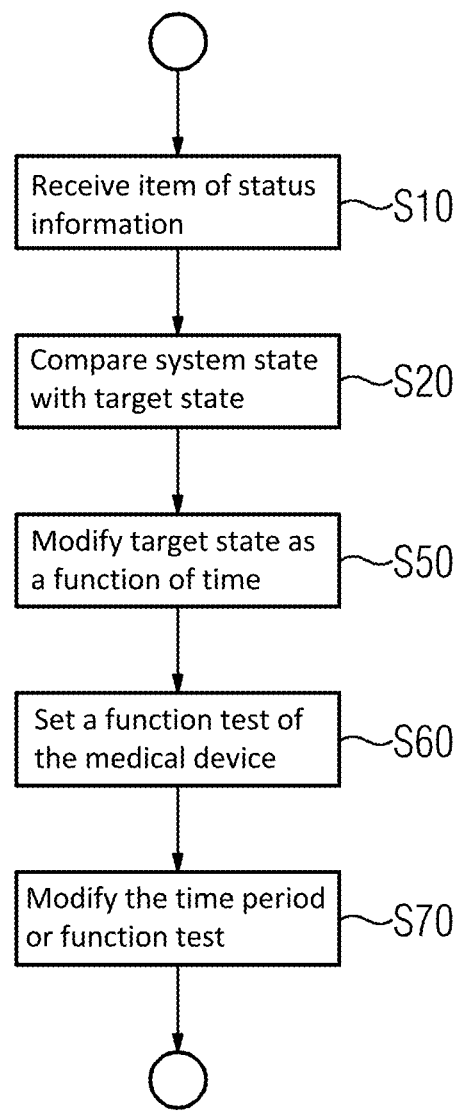

FAULT MONITORING APPARATUS AND METHOD FOR OPERATING A MEDICAL DEVICE

The present patent document claims the benefit of German Patent Application No. 10 2020 214 736.1, filed Nov. 24, 2020, which is hereby incorporated by reference in its entirety.

TECHNICAL FIELD

The disclosure relates to a fault monitoring apparatus for a medical device, a system including a fault monitoring apparatus and a medical device, and a method for operation. The medical device may be an imaging apparatus such as an X-ray device or magnet resonance tomography unit. The fault monitoring apparatus has a signal connection with the medical device and has a memory for storing a system state of the medical device. The fault monitoring apparatus receives status information from the medical device, compares the system state with a target state, and releases functions of the medical device.

BACKGROUND

Magnetic resonance tomography units are imaging apparatuses which, for imaging an examination object, align nuclear spins of the examination object with a strong external magnetic field and, by an alternating magnetic field, excite them to precession about this alignment. The precession and/or the return of the spins from this excited state into a state with less energy in turn generates, as a response, an alternating magnetic field which is received by way of antennas.

With the aid of magnetic gradient fields, a spatial encoding is impressed onto the signals, which then enables the received signal to be assigned to a volume element. The received signal is evaluated, and a three-dimensional imaging representation of the examination object is provided. In order to receive the signal, local receiving antennas, known as local coils, may be used. The local coils are arranged directly on the examination object in order to obtain an improved signal-to-noise ratio.

On account of the strong fields and high power of the excitation pulses, there is a risk that sensitive parts such as the input amplifier or even the patient will be endangered in the event of a malfunction. In medical devices such as X-ray devices or radiotherapy devices, a malfunction poses a danger to the patient.

Furthermore, a malfunction of a medical device may jeopardize or negate the success of an envisaged examination or treatment.

SUMMARY AND DESCRIPTION

The object of the present disclosure is therefore to render a medical device more reliable.

The object is achieved by a method, a fault monitoring apparatus, and a system as described herein. The scope of the present disclosure is defined solely by the appended claims and is not affected to any degree by the statements within this summary. The present embodiments may obviate one or more of the drawbacks or limitations in the related art.

The method is provided for operating a medical device. Medical devices may be imaging apparatuses (e.g., X-ray devices or magnetic resonance tomography units), radiotherapy apparatuses, or medical robots.

A fault monitoring apparatus is connected to the medical device via a signal connection. Here, the fault monitoring apparatus may be part of the medical device, (e.g., by way of a hardware module or software on a controller of the medical device), or may be realized as a separate unit. Furthermore, the fault monitoring apparatus has a memory for storing a system state of the medical device.

In one act of the method, the fault monitoring apparatus receives an item of status information from the medical device via the signal connection and stores the status information in the system state. The fault monitoring apparatus may query the status information by polling the medical device, for example, or may receive it passively. It is also conceivable for the fault monitoring apparatus to start a function test in order to ascertain the system state. The status information may indicate whether a function test has been executed successfully or with a fault message for a functional unit, whether a function test could not be executed for another reason, or whether another fault message is present for a functional unit.

It is conceivable for the fault monitoring apparatus to be configured to receive the system test of different medical devices or to set function tests in different medical devices. This enables the establishment of a device-independent service interface to different devices.

In one act, the fault monitoring apparatus compares the stored system state with a predetermined target state. The target state may have one or several entries pertaining to successfully executed function tests for one or several functional units of the system. Here, the comparison may include whether all these function tests are also indicated as successful in the system status. The comparison may also include that the system state has no further fault messages.

In a further act, the fault monitoring apparatus releases a function of the medical device, depending on the comparison, via the signal connection.

A release may take place when the predetermined target state has a successful function test, and it has been determined by way of the comparison with the system state that the function test has also been executed successfully.

It is also conceivable for a release to take place when all of a plurality of function tests indicated in the target state have been executed successfully. In addition, a release may be prevented when spontaneous faults have occurred and are indicated in the system state.

A weighting of the function tests is also conceivable, so that a function is only not released when the weighted function tests which have not yet been executed do not exceed a threshold value.

The method advantageously provides a preventive monitoring of the function of the medical device, thus increasing the reliability during operation.

The fault monitoring apparatus and the system that includes the medical device and the fault monitoring apparatus share the advantages of the method.

Further advantageous embodiments are specified with reference to the subclaims.

In one conceivable embodiment of the method, the fault monitoring apparatus modifies the target state as a function of time. It is conceivable, for example, for the fault monitoring apparatus to add further function tests which are to be executed successfully to the target state. Here, it is conceivable for these to be function tests, which are to be repeated regularly. Accordingly, the modification may take place periodically, (e.g., monthly, quarterly, or annually), depending on how often the function tests are repeated in order to provide a function of the medical device.

The modification of the target state advantageously makes it possible to plan maintenance activities and set them in advance. Here, periodic repetitions also enable sporadically occurring failures to be monitored.

In one possible embodiment of the method, in an act, the fault monitoring apparatus sets a function test of the medical device via the signal connection. The fault monitoring apparatus may start a function test of the medical device via the signal connection or specify a time-delayed execution, for example, at a predetermined point in time.

The fault monitoring apparatus may thus advantageously itself bring about the execution of function tests which have not already been executed successfully during operation.

In one conceivable embodiment of the method, in an act, the fault monitoring apparatus collects function tests which are due in a future, predetermined time period. These may be all function tests, which according to service planning are to be executed within the next month in order to provide a reliable function. In a further act, the function monitoring apparatus sets these collected function tests in a service window within the predetermined time period in the medical device. A service window may refer to a state of the device in which it is not being used for image acquisition and therefore all resources are available for function tests. The fault monitoring apparatus may also identify the service windows by way of inputs of an operator or by querying an internal or external database, for example, a file with planned operating times. Special operating states such as a start procedure or switch-off procedure, (e.g., a boot procedure, shutdown, ramp-up, or ramp-down), are also conceivable as service windows. The function tests are then automatically executed collectively as soon as the medical device assumes the corresponding state. It is also conceivable for the fault function apparatus to distribute the function tests over a plurality of service windows so as to keep the service windows short and avoid hindering operation.

The method advantageously also enables the function tests without additional interruptions to operation and manual interventions.

In one embodiment of the method, in an act, it is also possible for the fault monitoring apparatus or the medical device to delete a status for a successfully executed function test from the system status again after a predetermined time and/or after a function test with a negative result, so that a function associated with the function test is no longer released by the fault monitoring apparatus. A deletion of the "successfully executed" status from the system status may take place when the associated function test is set once again for execution.

In this way, it is advantageously possible to monitor the validity of a function test, for example if on account of the aging of components a repetition at time intervals is required in order to provide the function.

In one possible embodiment of the method, the fault monitoring apparatus has an input device for an operator, for example, an operator terminal or touchscreen. In a further act, the operator may modify the predetermined time period and/or the function tests. It is conceivable, for example, to move the times or provide for additional function tests. The fault monitoring apparatus may be configured not to permit a safety-related function test to be moved beyond a predetermined deadline.

Service may thus advantageously synchronize the automatic tests with planned service activities.

BRIEF DESCRIPTION OF THE DRAWINGS

The above-described characteristics, features, and advantages of this disclosure, as well as the manner in which these are realized, become clearer and more readily understandable in conjunction with the following description of the exemplary embodiments, which are explained in more detail in connection with the drawings.

FIG. 2 depicts an exemplary schematic flow diagram of an embodiment of the method.

DETAILED DESCRIPTION

Figure 1:
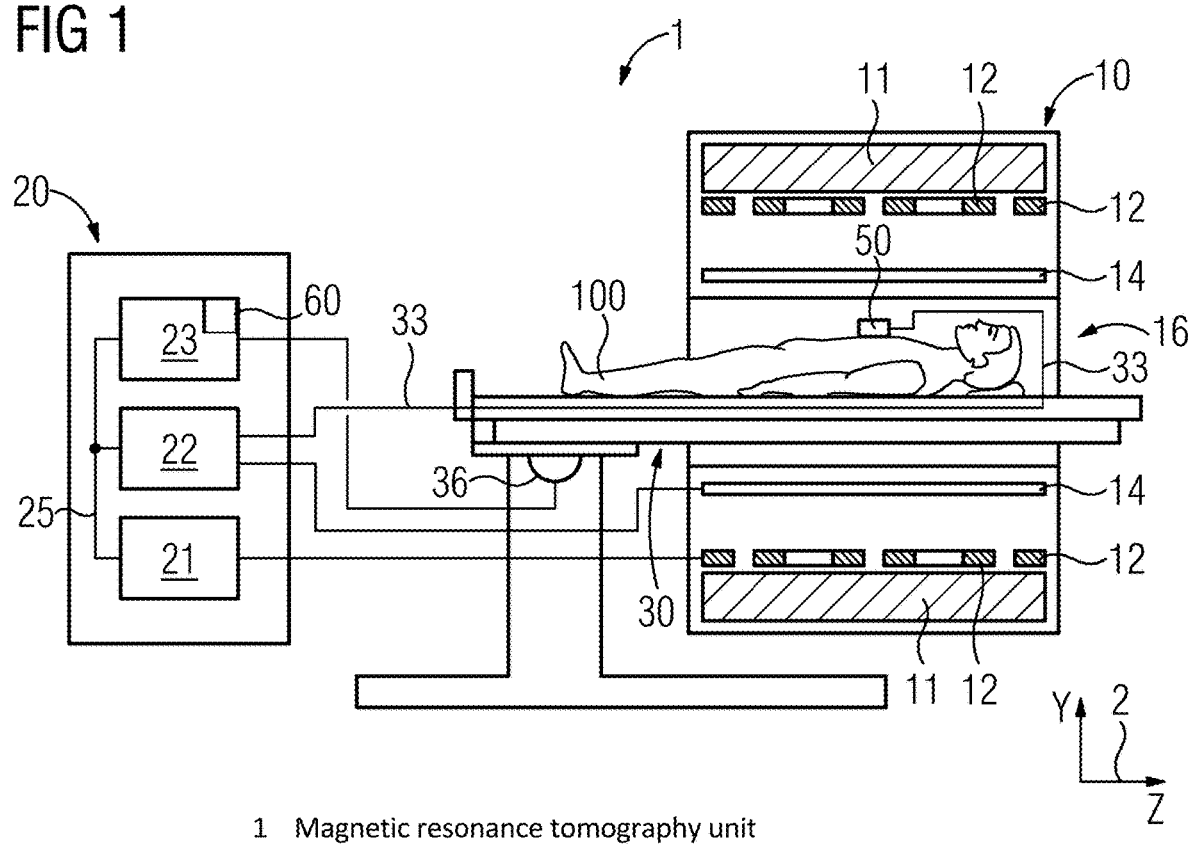
FIG. 1 depicts a schematic representation of a magnetic resonance tomography unit for carrying out the method according to an embodiment.

FIG. 1 depicts, as an embodiment of a medical device, a schematic representation of a magnetic resonance tomography unit 1 for carrying out the method.

The magnet unit 10 has a field magnet 11 that generates a static magnetic field BO for aligning nuclear spins of samples or of the patient 100 in a recording region. The recording region is characterized by an extremely homogeneous static magnetic field BO, wherein the homogeneity relates in particular to the magnetic field intensity or the absolute value. The recording region is virtually spherical in shape and is arranged in a patient tunnel 16 that extends in a longitudinal direction 2 through the magnet unit 10. A patient couch 30 may be moved in the patient tunnel 16 by the positioning unit 36.

The field magnet 11 may be a superconducting magnet that may provide magnetic fields having a magnetic flux density of up to 3 T, or even more in more recent devices. For lower field intensities, permanent magnets or electromagnets with normally conducting coils may also be used.

Furthermore, the magnet unit 10 has gradient coils 12 configured to overlay the magnetic field BO with variable magnetic fields in three spatial directions for the purpose of spatially differentiating the acquired mapping regions in the examination volume. The gradient coils 12 may be coils made of normally conducting wires which may generate mutually orthogonal fields in the examination volume.

The magnet unit 10 also has a body coil 14 configured to emit a radio frequency signal fed via a signal line into the examination volume and to receive resonance signals emitted from the patient 100 and to pass them on via a signal line. In the following, the term "transmitting antenna" refers to an antenna via which the radio frequency signal is emitted in order to excite the nuclear spins. This may be the body coil 14, but also a local coil 50 with a transmitting function.

A control unit 20 supplies the magnet unit 10 with the various signals for the gradient coils 12 and the body coil 14 and evaluates the received signals.

Accordingly, the control unit 20 has a gradient controller 21 configured to supply the gradient coils 12 via supply lines with variable currents which provide the desired gradient fields in the examination volume in a temporally coordinated manner.

Furthermore, the control unit 20 has a radio frequency unit 22 configured to generate a radio frequency pulse with a predetermined temporal sequence, amplitude, and spectral power distribution for the excitation of a magnetic resonance of the nuclear spins in the patient 100. Pulse powers in the kilowatt range may be achieved in this case. The excitation signals may be radiated into the patient 100 via the body coil 14 or also via a local transmitting antenna.

A controller 23 communicates with the gradient controller 21 and the radio frequency unit 22 via a signal bus 25.

A local coil 50 is arranged as a receiving antenna on the patient 100 and is connected to the radio frequency unit 22 and its receiver via a connecting lead 33. It is also conceivable for the body coil 14 to be a receiving antenna.

The magnetic resonance tomography unit 1 has a fault monitoring apparatus 60. In the exemplary embodiment shown, the fault monitoring apparatus 60 is implemented as a software function on the controller 23. A dedicated hardware unit with its own processor would however also be conceivable so as also to be able to test the function of the controller. Also conceivable is a function monitoring apparatus 60 that monitors several medical devices via signal connections thereto. The fault monitoring apparatus 60 may have a control element in the medical devices which permits a full test of the medical device, including the controller.

FIG. 2 depicts a schematic flow diagram of an exemplary embodiment of a method.

In act S10, the fault monitoring apparatus 60 receives an item of status information from the medical device and stores the status information as a system state in a memory. If, for example, the fault monitoring apparatus 60 is embodied as a program on the controller 23, the status information from the controller may be provided by writing to a shared memory. It is also conceivable for the status information to be received via the signal bus 25 of the radio frequency unit 22 or the gradient unit 21. The fault monitoring unit may also be embodied as separate hardware with its own processor and memory, which are connected via the signal bus 25.

It is also conceivable for the fault monitoring apparatus 60 to be remote and connected to the medical device via a signal connection. Here, a control element of the fault monitoring apparatus 60 may be arranged in the medical device in order to form a bridge and enable function tests relating, for example, to the controller 23 of the medical device.

In further act S20, the fault monitoring apparatus 60 compares the stored system state with a predetermined target state. The target state may indicate which function tests must be successfully executed at a predetermined point in time in order to provide a reliable function of the medical device. The predetermined target state may also have the absence of predetermined fault messages.

The comparison may be a logical operation such as XOR in order to output whether all function tests required at the point in time of the comparison have been executed successfully and/or no system-critical fault messages are present.

Depending on the comparison, in act S30, the fault monitoring apparatus 60 releases one function or several functions of the medical device. It is conceivable for example for the function test to check a power sensor of the radio frequency sensor which is used to provide adherence to the SAR limit values. For the function test, the radio frequency unit 22 may provide a defined output signal in order to check a calibration of the sensor, which is not possible during ongoing operation. If it has not yet been too long since the last check, wherein the time interval between function tests depends on the complexity of the function being checked and the aging of the components and indicated by a successfully executed function test in the system state, the function of the high frequency transmitter may be released by the fault monitoring apparatus.

In one embodiment of the method, in act S50, the target state may be modified as a function of time. This may take place by way of the fault monitoring apparatus itself, but a modification by the system controller 23 or an external service center via a signal connection is also conceivable. In particular, it is conceivable for a modification of the target state in act S40 to take place periodically, in other words for the act S40 to be repeated at regular, predetermined time intervals. Here, the time intervals may depend on an aging or a fault probability of components of the medical device. It is conceivable for example for the time intervals to be less than one week, between one week and one month, between one month and one quarter, or between one quarter and one year.

Here, the modification of the target state may also include deleting the status for a successfully executed function test in the system status because this function test must be repeated on account of a possible aging of components. To provide safety, the function may then no longer be used after expiration of a period of validity of the function test, which may depend on the type of the components concerned or the frequency of loading, unless the successful repeat function test is entered in the system status. This repeat function test may in turn be triggered by the setting of the function test as described below.

Here, it is also conceivable for the act S50 of modifying the target state to take place before the acts S10 to S30.

In one embodiment of the method, in act S60, the fault monitoring apparatus 60 sets a function test of the medical device via the signal connection. Here, setting may mean both that the function test is triggered directly and also that it is executed with a time delay. This may mean an execution at a predetermined point in time or time period, or a conditional action in conjunction with an operating state of the medical device. It may be a combination of time period and condition, for example, a boot procedure of the medical device in the next two months, or between two other predetermined future points in time. Here, it is also conceivable for the fault monitoring apparatus 60 or the control unit 20 to also delete the successful status for the function test in the system status at the same time as setting the function test.

Here, it is conceivable in particular for the fault monitoring apparatus 60, in act S40, to collect function tests which are to be executed in a predetermined time period and, in the act S60, to set them in a service window within the predetermined time period in the medical device. Here, service window is understood to mean a time period in which the medical device is not required for examinations or treatments and therefore function tests may be executed without disrupting operation. In particular, special operating states such as a boot process or start procedure, shut-down or switch-off procedure of the medical device or a ramp-up or ramp-down of the magnet in a magnetic resonance tomography unit are considered. Function tests that require these special operating states may be tests of a monitoring of the supply voltage or of monitoring timers (watchdogs) of the medical device, because these may result in a reboot in the case of a successful function test.

It is furthermore possible for the fault monitoring apparatus to have an input device for an operator. In one embodiment of the method, in act S70, the operator may modify the predetermined time period and/or the function tests via the input device of the fault monitoring apparatus. In this way, the operator may influence the execution of the function tests according to administrative specifications within a tolerance window in which the absence of a successful function test does not yet jeopardize safety. The fault monitoring apparatus may be configured to reject inputs or to acknowledge them with a warning if they fall outside a tolerance window, in particular thereafter, and would reduce safety.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a medical device, the method comprising:
    receiving, by a fault monitoring apparatus, an item of status information from the medical device and storing the item of status information in a system state of a memory of the fault monitoring apparatus, wherein the fault monitoring apparatus is connected to the medical device via a signal connection;
    comparing, by the fault monitoring apparatus, the stored system state with a predetermined target state, wherein the predetermined target state indicates at least one function test that must be successfully executed at a predetermined point in time in order to provide a reliable function of the medical device;
    releasing at least one function of the medical device via the signal connection when the comparing has confirmed that the stored system state has successfully executed the at least one function test indicated by the predetermined target state; and
    operating the at least one released function of the medical device.

2. The method of claim 1, wherein the medical device is an imaging apparatus.

3. The method of claim 2, wherein the imaging apparatus is an X-ray device or magnetic resonance tomography unit.

4. The method of claim 1, further comprising:
    modifying, by the fault monitoring apparatus, the target state as a function of time.

5. The method of claim 4, wherein the fault monitoring apparatus modifies the target state periodically.

6. The method of claim 4, further comprising:
    setting, by the fault monitoring apparatus, a function test of the medical device via the signal connection.

7. The method of claim 4, further comprising:
    collecting, by the fault monitoring apparatus, function tests which are due in a future, predetermined time period; and
    setting the function tests in a service window within the predetermined time period in the medical device.

8. The method of claim 7, wherein the service window is a start procedure or switch-off procedure of the medical device.

9. The method of claim 7, further comprising:
    modifying the predetermined time period and/or the function tests via an input device of the fault monitoring apparatus.

10. The method of claim 1, further comprising:
    setting, by the fault monitoring apparatus, a function test of the medical device via the signal connection.

11. The method of claim 1, further comprising:
    collecting, by the fault monitoring apparatus, function tests which are due in a future, predetermined time period; and
    setting the function tests in a service window within the predetermined time period in the medical device.

12. The method of claim 11, wherein the service window is a start procedure or switch-off procedure of the medical device.

13. The method of claim 11, further comprising:
    modifying the predetermined time period and/or the function tests via an input device of the fault monitoring apparatus.

14. A fault monitoring apparatus for a medical device, the fault monitoring apparatus comprising:
    a signal connection with the medical device,
    wherein the fault monitoring apparatus is configured to:
        receive results of self-tests of the medical device and store the results of the self-tests in a system state of the medical device;
        compare the system state with a predetermined target state having a successfully executed function test, wherein the predetermined target state indicates at least one function test that must be successfully executed at a predetermined point in time in order to provide a reliable function of the medical device; and
        release at least one function of the medical device when the comparison has confirmed that the system state has successfully executed the at least one function test indicated by the predetermined target state.

15. The fault monitoring apparatus of claim 14, wherein the fault monitoring apparatus is further configured to modify the target state as a function of time.

16. A system comprising:
    a fault monitoring apparatus; and
    a magnetic resonance tomography unit connected to the fault monitoring apparatus via a signal connection,
    wherein the fault monitoring apparatus is configured to:
        receive results of self-tests of the magnetic resonance tomography unit and store the results of the self-tests in a system status of the magnetic resonance tomography unit;
        compare the system state with a predetermined target state having a successfully executed function test, wherein the predetermined target state indicates at least one function test that must be successfully executed at a predetermined point in time in order to provide a reliable function of the magnetic resonance tomography unit;
        release at least one function of the magnetic resonance tomography unit when the comparison has confirmed that the system state has successfully executed the at least one function test indicated by the predetermined target state; and
        set a function test in the magnetic resonance tomography unit.

17. A non-transitory computer program product configured to be loaded directly into a processor of a programmable control unit of a system, wherein the computer program product, when executed on the control unit, is configured to cause the system to:
    receive, by a fault monitoring apparatus of the system, an item of status information from a medical device and store the item of status information in a system state of a memory of the fault monitoring apparatus, wherein the fault monitoring apparatus is connected to the medical device via a signal connection;

compare, by the fault monitoring apparatus of the system, the stored system state with a predetermined target state having a successfully executed function test, wherein the predetermined target state indicates at least one function test that must be successfully executed at a predetermined point in time in order to provide a reliable function of the medical device;

release at least one function of the medical device via the signal connection when the comparison has confirmed that the stored system state has successfully executed the at least one function test indicated by the predetermined target state; and operate the at least one released function of the medical device.

\* \* \* \* \*